United States Patent [19]
Martin et al.

[11] Patent Number: 5,515,872
[45] Date of Patent: May 14, 1996

[54] CLAMP FOR NASOLACRIMAL SAC OCCLUSION DURING ADMINISTRATION OF OCULAR MEDICATION

[75] Inventors: Neil F. Martin, Potomac; Howard N. Robinson, Lutherville, both of Md.

[73] Assignee: Bloom & Kreten, Towson, Md.; a part interest

[21] Appl. No.: 320,858

[22] Filed: Oct. 11, 1994

[51] Int. Cl.$^6$ .................................................... A61B 19/00
[52] U.S. Cl. ...................... 128/898; 606/204.15; 606/157
[58] Field of Search ................................ 606/204.45, 201, 606/151, 157, 204.15, 204.25, 204.35

[56] References Cited

U.S. PATENT DOCUMENTS

| | | | |
|---|---|---|---|
| 186,422 | 1/1877 | Hackett et al. | |
| 580,954 | 4/1897 | Ray | 606/157 |
| 598,467 | 2/1898 | Carence | |
| 2,274,997 | 3/1942 | Thurman | |
| 2,620,793 | 12/1952 | Gollubier | |
| 3,426,751 | 2/1969 | Radewan | 606/215 |
| 4,033,342 | 7/1977 | Lake | 606/201 |

OTHER PUBLICATIONS

Lally, Steven, "The Case of The Non–Perspiring Perambulator; Perspiration Dysfunction; Includes Related Article on Eye–Drop Side Effects" Prevention. vol. 42; No. 8, p. 120; ISSN: 0032-8006 Aug. 1990.

Gerber et al; "Systematic Drug Interactions With Topical Glaucoma Medications"; Survey of Ophthalmology; vol. 35, No. 3, Nov.–Dec. 1990; pp. 205–218.

Huang et al; "Punctal Occlusion and Topical Medications for Glaucoma"; American Journal of Ophthalmology; Feb. 1989; pp. 151–154.

Physicians' Desk Reference for Nonprescription Drugs; 14 Edition; 1993; pp. 697–699.

Herrick; "Collagen Implants Said to Help DX of Keratoconjunctivitis Sicca", Ophthalmology Times; vol. 10, No. 23; Dec. 1, 1985.

Urtti et al; "Minimizing Systemic Absorption of Topically Administered Ophthalmic Drugs"; Therapeutic Review; Survey of Ophthalmology; vol. 37, No. 6; May–Jun. 1993; pp. 435–456.

Collignon; "Cardiovascular and Pulmonary Effects of Beta–Blocking Agents: Implications for Their Use in Ophthalmology (Summary)"; Survey of Ophthalmology; vol. 33, Supplement, Apr. 1989, pp. 455–456.

Muenzler; "The Dry Eye–A working Outline of Etiology, Symptoms, Diagnosis, and Treatment"; Geriatric Ophthalmology, Jan.–Feb. 1986.

*Primary Examiner*—Stephen C. Pellegrino
*Assistant Examiner*—Glenn Dawson
*Attorney, Agent, or Firm*—Leonard Bloom

[57] ABSTRACT

The invention herein described involves a clamp placed over the bridge of the nose to apply pressure over the fossa of the nasolacrimal sac, prior to ocular medication, to seal the nasolacrimal sac, and thereby prevent drainage of medicament away from the eye.

3 Claims, 6 Drawing Sheets

CLAMP FOR NASOLACRIMAL SAC OCCLUSION DURING ADMINISTRATION OF OCULAR MEDICATION

FIELD OF THE INVENTION

The invention relates to devices that clip or clamp to the bridge-area of the nose to exert pressure and thereby prevent fluid from the eyes from flowing away during ocular medication.

BACKGROUND OF THE INVENTION

Ophthalmologists have recognized that medicaments administered to the eye by drops drain from the eye and are absorbed into the blood stream. This presents a two fold problem. First, the drug absorbed from the eye to the blood stream can cause undesirable side-affects. Second, because the eyedrop medication quickly drains from the eye into the blood stream, contact time between the medicament and the eye is undesirably shortened, with the result that the medicine does not have the desired affect on the condition being treated.

Ocular medications, when instilled into the eye drain away from the eye through the lacrimal system into the nasopharynx. This process takes several minutes depending upon the viscosity of the medication instilled. Drainage of medication away from the eye decreases contact time with the conjunctiva and cornea, and hence decreases ocular absorption. The drainage through the lacrimal system removes the drops from the eye and places the drops in contact with the nasal mucosa. The nasal mucosa allows for rapid absorption of medications into the blood stream. Certain medications can cause generalized side effects. Glaucoma medications, especially the class called beta-blockers, have been associated with significant morbidity, as well as, mortality from cardiovascular and pulmonary side effects.

Various solutions to the problem of systemic absorption of medicaments from the eye into the blood stream have been proposed in the medical literature.

Huang et al—American Journal of Ophthalmology, Vol. 107, February 1989 pages 151–155 discuss several methods for maximizing contact time between the eye and medication. In the article they state that, "... most topical ophthalmic medications with intraocular sites of action penetrate the eye through the cornea, conjunctiva, or sclera. The amount of medication absorbed is influenced by the amount of contact time between the medication and the ocular surfaces. Most of an eyedrop is lost to drainage within 15 to 30 seconds after instillation, which includes rapid drainage of 80% or more of the volume through the nasolacrimal system. Inhibition of this rapid drainage may lengthen the contact time of the medication with the eye and increase its absorption and efficacy.

Inhibition of drainage through the nasolacrimal system may be achieved by manual occlusion with a fingertip, by placing plastic or collagen plugs into the puncta, or by permanently closing the puncta with cautery or laser. Nasolacrimal occlusion with fingertip pressure as a means of increasing ocular absorption of topical ocular medications has been proposed. Many patients, however, are unable to practice proper manual nasolacrimal occlusion."

Urttic et al—Survey of Ophthalmology Vol. 37, No. 6 May—June 1993 pages 435–456 discusses in a review article methods for minimizing the systemic absorption of topically administered ophthalmic drugs. One of the ways suggested to increase ocular absorption and minimize systemic absorption was punctual occlusion, to block ocular drainage of the eyedrop from the conjunctival sac. This method involves applying the drops and pressing the inner ocular corners near the bridge of the nose with the fingers for 30 seconds to several minutes.

Gerber et al—Survey of Ophthalmology, Vol. 35 Number 3, November—December 1990, pages 205–218 states that:

"Topically applied ophthalmic medications can attain sufficient serum levels via absorption into conjunctival, nasal, oropharyngeal and gastrointestinal mucosa to have systemic effects and thereby interact with other drugs. In fact, topical administration to the eye has been likened to intravenous rather than oral administration because a high percentage of the absorbed drug avoids hepatic first-pass metabolism; thus, drugs administered by this route can attain higher levels relative to dose than if administered orally.

It is important to remember that even where the potential for drug interaction exists, there are methods to reduce systemic absorption. Nasolacrimal occlusion, a technique in which digital pressure on the periphery of the nasolacrimal drainage system obstructs drainage to the nasopharyngeal mucosa, has been shown to significantly decrease systemic absorption. Eyelid closure for five minutes following drug application also achieves the same purpose by inhibiting nasolacrimal pump action."

The eyelid closure method of nasolacrimal occlusion involves the steps of tilting the head back and gently pulling down the eyelid to form a "V" pocket between the eye and the lower lid; placing drops of medicine in the eye; closing eyes and keeping head tilted back for 30 seconds to assure absorption of medication into the eye.

Methods involving the combination of punctual occlusion along with eyelid closure are recommended by many ophthalmologists.

Muenzler—Geriatric Ophthalmology Vol. 2 (1), January/February 1986, pages 19–23 in a discussion of the treatment for "dry eye" suggests another method of punctual occlusion using punctum plugs. Punctum plugs made of silicon supplied by Eagle Vision used to occlude the punctum and canaliculus are available to ophthalmologists.

Collagen implants have been experimentally implanted into the canaliculus as temporary implants to test for various abnormalities of the eye, such as, redness, burning, tearing, dry eye conjunctivitis, etc. If the complained of condition improves with the implant, the doctor considers permanent closure of the canaliculus. (Ophthalmology Times, Vol. 10 No. 23 Dec. 1, 1985).

A review of the literature indicates that the medical profession has recognized a number of ways to prolong contact time between medication and the eye, however none of the prior art has recognized applicants' occlusive device or method of employing such a device to prolong contact time between the eye and the medicament applied to the eye.

Prior art patents describe various clamping devices

Carence in U.S. Pat. No. 598,467 describes a "Nostril-Protector" which is designed to externally close the nostrils and prevent the entrance of dust carried by the atmosphere from entering the nose. The Carence device has a spring actuated clip which grasps the central partition or cartilage dividing the two nostrils and thereby positions attached plates to close the nostrils. Thus, dust is prevented from entering the nose.

Hackett et al in U.S. Pat. No. 186,422 discloses a spring-like device for use by swimmers with ear stoppers and nose pads. The ear stoppers on the spring frame occlude the ears, and nose pads on the spring frame seal the nostrils. In this way, water is prevented from entering the nose and ears.

U.S. Pat. No. 2,274,997 to Thurman illustrates a nose plug which is inserted into the nose to keep water out of nasal passages during swimming. The device has a spring-like portion attached to laterally projecting integral arms which are engageable with the vomer portions of the nose for securing nose plugs in position to keep water out of the nasal passages.

Gollubier in U.S. Pat. No. 2,620,793 depicts a U-shaped nose clip for use by swimmers to prevent water or foreign matter from entering the nose. The nose clip can be made of a single U-shaped piece of resilient wirelike material. The nose clip can be coated with rubber or plastic. The coating serves to prevent corrosion of the wirelike material. Further, the coating prevents the clip from scratching the skin when the clip is applied or removed from the nose, as well as, preventing the clip from slipping during vigorous swimming activity.

In a modified embodiment, the Gollubier device has two pivotally connected arms. The bottom portion of the pivotally connected arms are spring actuated and when squeezed together open the top portion of the pivotally attached arms for application to the nose. Release of the bottom arms squeezes the top arms to seal the nasal passages.

A clip for sealing the nostrils is taught by Claudius in U.S. Pat. No. 2,015,617, and Browne in U.S. Pat. No. 2,488,616. The clip disclosed in both of these patents seals the nostrils and prevents air from entering.

A mechanical clamp-like device for shaping the nose is taught by Tanikaw in U.S. Pat. No. 2,757,665.

Freeman (U.S. Pat. No. 3,949,750) and MacKeen et al (U.S. Pat. No. 4,915,684) disclose punctum plugs for insertion into the punctual apertures of the eyes. Freeman's device blocks drainage of lacrimal fluid. The device of MacKeen et al modulates and controls the flow of lacrimal fluid.

U.S. Pat. No. 580,954 to Ray discloses a device for clamping noses to correct nasal deformity.

While clips per se are old, and have been placed on various parts of the body, including the nose, none of the prior art cited shows a clip or clamp applied to the bridge of the nose to exert an exact pressure over the fossa of the nasolacrimal sac to prevent tears from flowing and thereby carrying away medication topically applied to the eyes.

SUMMARY OF THE INVENTION

This invention has as an object the production of an efficient way of prolonging contact time between the eye and medication applied to the eye.

An additional object is to produce a device which is easy to apply and prolongs eye contact time with the medication.

The purpose of the current invention is to provide consistent and sustained occlusion of the nasolacrimal sac, with a clip over the bridge of the nose to achieve prolonged contact between the applied medication and the eye.

The present invention describes a clip or clamp to go over the area of the bridge of the nose to exert pressure over the fossa of the nasolacrimal sac, thereby preventing tears from flowing away from the eye, through the punctae, into the "tear" or nasal lacrimal duct. The sealing of the nasolacrimal duct is known as nasolacrimal occlusion (NLO). This occlusion maximizes contact time and ocular absorption of topical medications and minimizes systemic side effects of topical ocular medications.

Many designs of the clamp are possible, and in construction they can be made of rubber, plastic, or metal, or a combination of these. The general shape of the device could be a "U" shape with prominences at the position where the lacrimal sac is located and occlusion is to take place. The inside of the clamp could be tapered to fit comfortably at the bridge of the nose, as well as, to be better positioned for achieving good nasolacrimal occlusion. The outer surface of the clamp could be corrugated to allow for easier application and removal. In addition to a one-piece design, multiple-piece designs could be created with a spring at the apex of the "U" to allow for flexing and application of the clamp. The spring could be of variable or adjustable tension. An alternative design would allow for stick-on nose pads similar to those used for spectacles. The nose pads could be placed on the arms of the clip to adjust the fit of the clip to an individual's anatomy. Alternatively, the inside of the "U" or arms could be widened to provide a generalized pressure over a larger area at the bridge of the nose, like that of the tip of a finger. This would allow for occlusion with a less exact placement of the clip. An alternative design would have a "U" shaped clip in an outer mold, placed over the bridge of the nose and be filled with a rubber-like material, thereby producing a customized casting to fit the individual's nasal shape. The clip could be of a design that the patient alone could fit or the clip could be adjustable to allow fitting by an eye care professional or optician. Alternatively, the patient could be supplied with a series of clips and told to use the one which fits best, or the doctor could fit the patient with the clip which fits best.

A most important consideration for this invention is the pressure to be exerted by the nasal clip. The clip has to be constructed in such a way as to exert enough pressure to occlude the nasopharynx and not so much pressure as to cut-off the blood supply and thereby produce ischemia.

In the preferred method of use, the nasolacrimal clip or clamp is applied first over the bridge of the nose and then the eyedrop is applied to the eye. By applying the clip first and then applying the drops, advantage is taken of the fact that the duct is sealed prior to application of the drops. Since sealing of the duct takes place prior to instilling the eyedrops, maximum contact time between medication and eye takes place. In methods such as finger punctual occlusion, where the drop is applied first and then the finger applied to the bridge of the nose to prevent drainage, valuable time is lost between the application of the eye drop and the finger-sealing of drainage.

A specific embodiment of this invention involves a nasolacrimal clamp for placement over the bridge of the nose to apply pressure over the fossa of the nasolacrimal sac, prior to ocular medication. The clamp has two arms having inner surfaces for fitting over the bridge of the nose, with each of said arms of the clamp supplying a predetermined pressure to the nasolacrimal sac, to occlude drainage of medicament, without occluding the blood supply and causing ischemia. The clamp can be resilient and arcuate in form. The predetermined pressure supplied by the two arms can be created on the two inner surfaces of the clamps by the resiliency of the material from which the clamp is made. Alternatively, the predetermined pressure supplied by the two arms can be created on the inner surfaces of the arms by a spring.

In a specific embodiment the clamp has on the inner surface of each arm attached adjustable pads, such that the pads when adjusted on the inner surface of the arms apply pressure at the exact point over the fossa of the nasolacrimal sac.

In a unique embodiment of this invention the clamp is attached to eyeglasses designed to accept eyedrop medication applied to the eye.

A special embodiment of this invention envisions embedding the clamp in a flexible molded positioning device which has been molded to fit the shape of the bridge of the nose and with the clamp in such a position in the molded device to positively seal the nasolacrimal sac and thereby prevent drainage of medicament. By the use of the flexible molded positioning device with the nose clamp embedded therein, the clamp will be accurately placed over the fossa, and the exact amount of pressure can be built into the clamp to assure the effective sealing of the fossa of the nasolacrimal sac without causing ischemia.

The inventors expect to dispense the clamp of this invention with medications applied to the eye; and specifically in a package containing eyedrops. In the most preferred embodiment, the package will be a dispensing package containing a container of eyedrops and an eyedropper. The clip could be supplied in a sterile wrapper put into the package along with the eyedrops. This method of dispensing would involve a kit or package containing the eyedrop medicament along with the clip. Directions for use could be inserted in the package as a package insert.

In specific use, the disclosed invention involves a specific improved method for applying medication to the eye, comprising applying a clamp to the bridge of the nose to apply a predetermined pressure over the area of the fossa of the nasolacrimal sac to occlude drainage of medicament from the eye, and then administering medication to the eye. Specifically that medication can be applied in the form of an eyedrop.

GENERAL DESCRIPTION OF THE PREFERRED EMBODIMENTS

Figure 1:
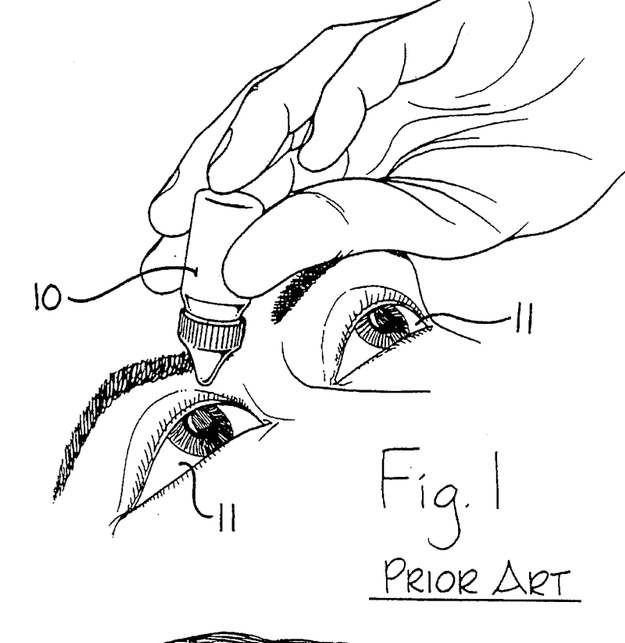
FIG. 1 illustrates the conventional prior art method of applying eyedrops to the eye.
Figure 2:
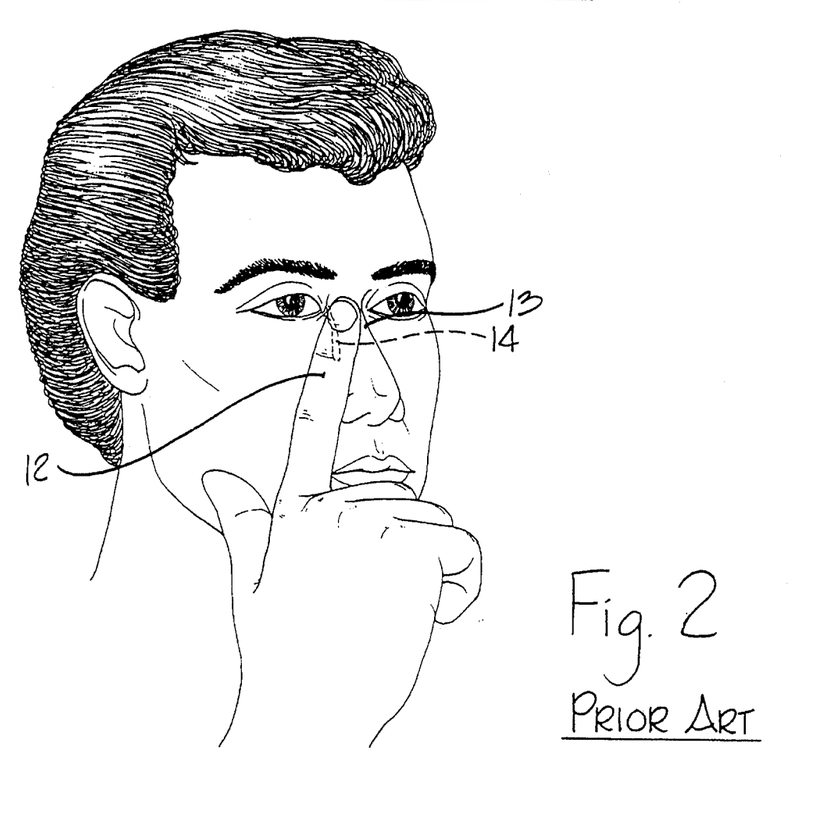
FIG. 2 illustrates punctual occlusion by the use of the finger as done by the prior art.

With reference to FIGS. 1 and 2 eyedrops 10 are applied to eyes 11 (FIG. 1) and then placement of the finger 12 to the bridge of the nose 13 (FIG. 2) to occlude the nasolacrimal system 14 as done by the prior art. As set forth above this system was inefficient.

Figures 3, 4:
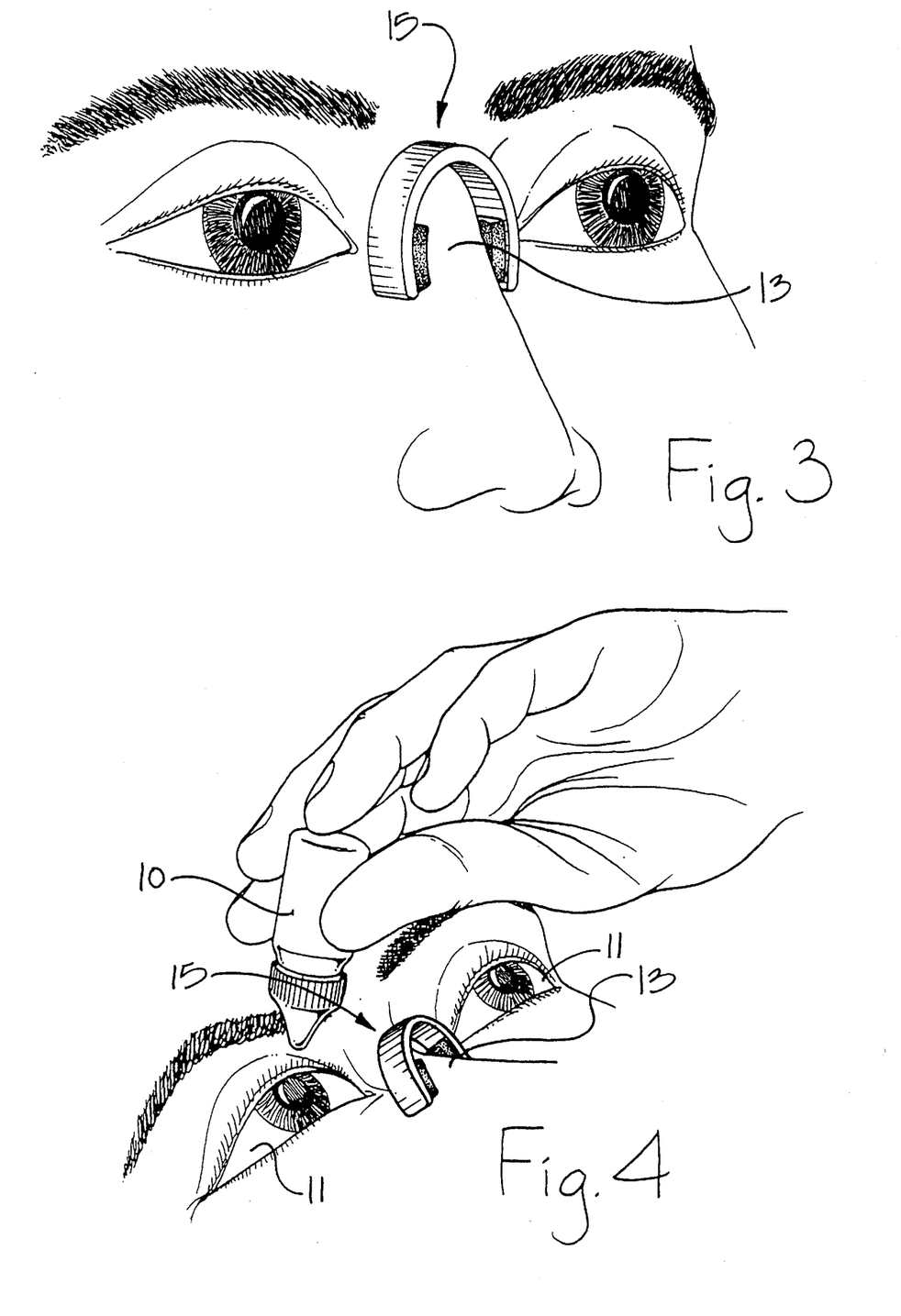
FIG. 3 is a view illustrating the nasolacrimal clamp of this invention applied to the bridge of the nose.
FIG. 4 is a view illustrating the application of eye drops with the clamp in place.
Figure 5:
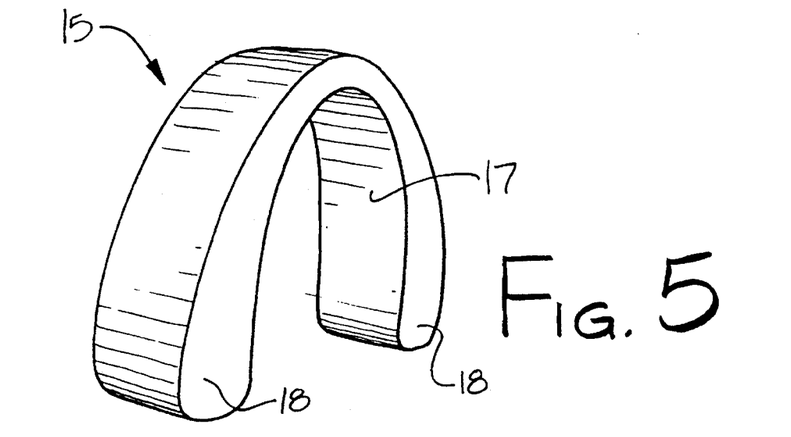
FIG. 5 is a view illustrating a simple clamp used in this invention.
Figure 6:
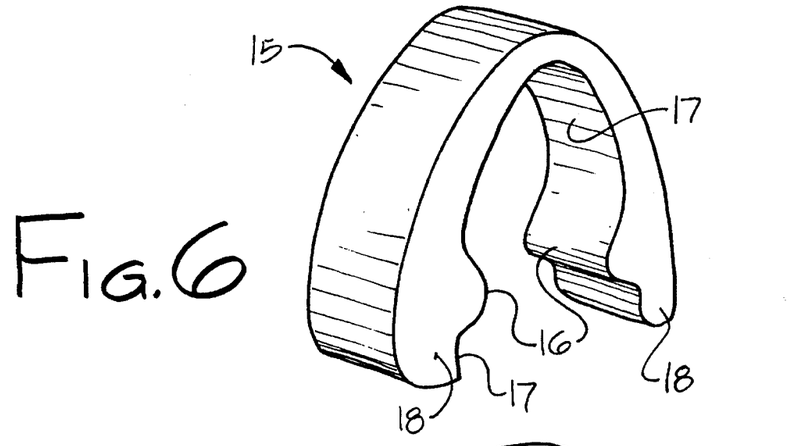
FIG. 6 is a view illustrating a modification of the clamp with projections for applying pressure.

In FIGS. 3 and 4 the clamp 15 placed over the bridge of the nose 13 occludes the nasolacrimal system (not shown) (FIG. 3) allowing eyedrops 10 to be applied FIG. 4 with maximum contact time between medication and the eye 11.

Several embodiments envisioned by this invention are exemplified in the drawings (FIGS. 5–16).

A clamp or clip 15 for applying generalized pressure over the fossa of the nasolacrimal sac (FIG. 5) can be molded of rubber or plastic; or can be made of spring metal covered by rubber or plastic.

The clamp can be a one-piece molded clamp 15 (FIG. 6), with projections 16 on the inside surface 17 of the two legs 18 of the clamp for applying pressure to the nasal lacrimal duct.

Figure 7:
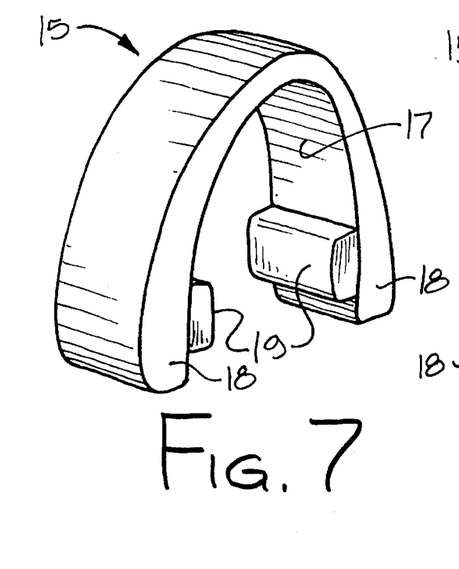
FIG. 7 is a view illustrating a modification of the clamp with removable pads for applying pressure.
Figure 8:
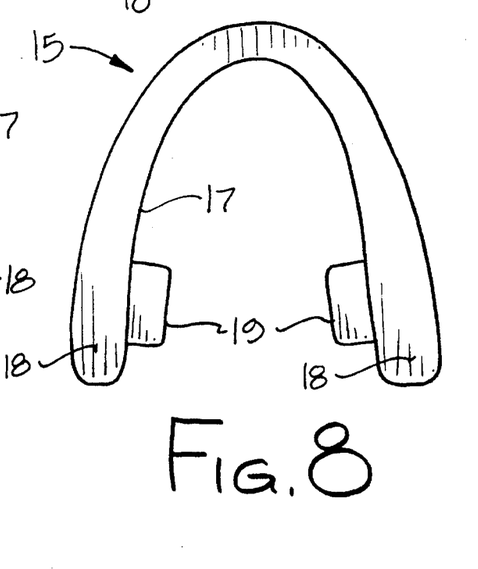
FIG. 8 is an elevational view thereof.

With reference to FIGS. 7 and 8, the clamp 15 has adjustable stick-on pads 19. The adjustment of the pads 19 on the legs of the clamp 18 will allow the patient or doctor to adjust the placement of the pads 19 to fit exactly over fossa of the nasolacrimal sac thus assuring maximum occlusion once the clamp is applied.

The projections or stick-on pads 19 can be hollow and air-filled, or hollow and filled with a gel. Alternatively, the pads could be made of soft rubber or soft plastic. The consistency of the stick-on pads 19 should be such as to make application of the clamp 15 as comfortable as possible for the patient, bearing in mind the need for proper occlusion. Comfort of application is particularly important because of the desire to ensure that the patient employ the clamp 15 religiously.

Figure 9:
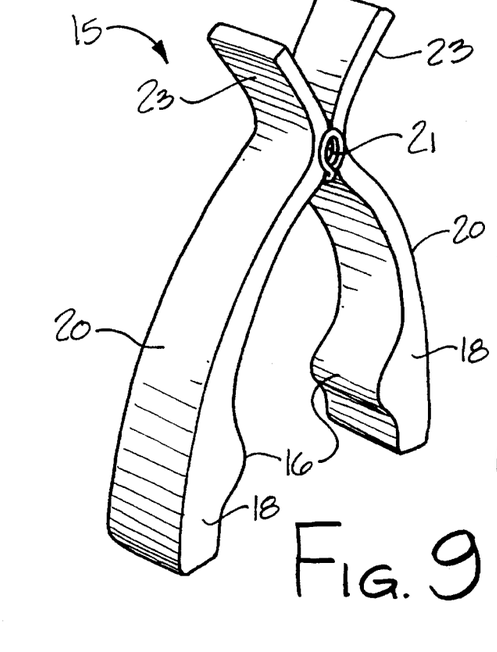
FIG. 9 is a view illustrating a spring actuated clamp.
Figure 10:
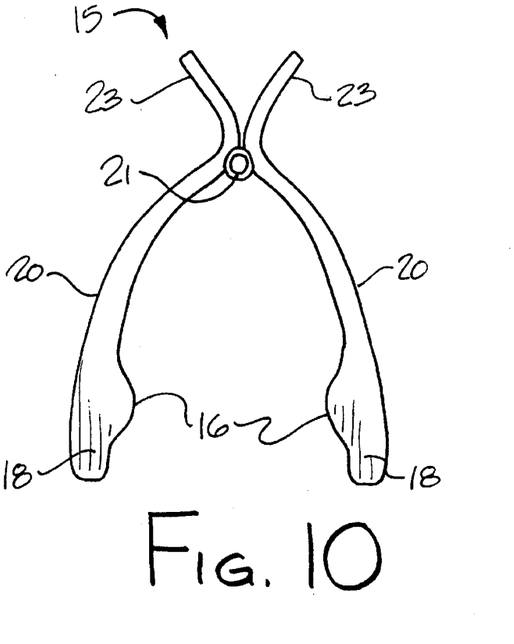
FIG. 10 is an elevational view thereof.
Figure 11:
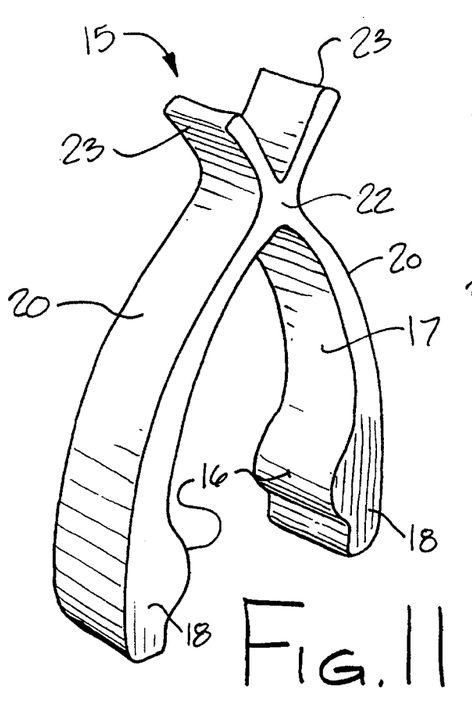
FIG. 11 is an illustration of a resilient plastic clamp.
Figure 12:
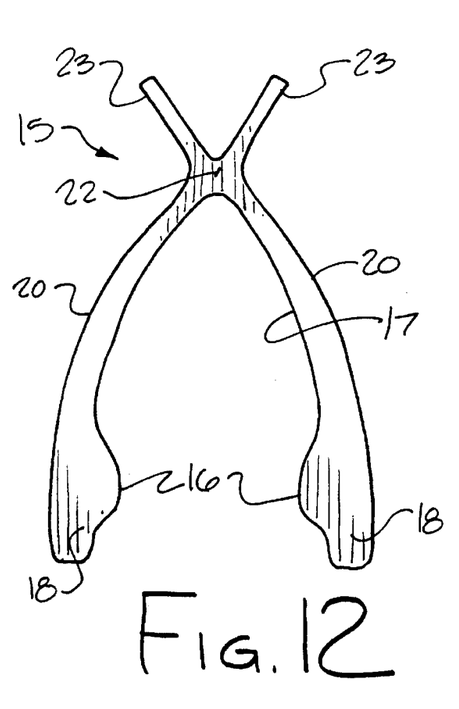
FIG. 12 is an elevational view thereof.

In FIGS. 9–12 the nasolacrimal clamp 15 is tong-like 20. The two legs of the clamp 18 (FIGS. 9–10) are held together by a spring 21 which provides pressure when the clamp 15 is applied to the fossa of the nasolacrimal sac. FIGS. 11–12 depict the tong-like clamps 15 made of flexible metal or plastic, etc. In this latter embodiment pressure is applied through the flexibility of the material 22, such as plastic, rather than a spring action 21 (FIGS. 9–10). Pressure grips 23 (FIGS. 9–12) at the top of the clamp 15 aid in opening the legs of the clamp 18 for placement of the clamp on the bridge of the nose.

Figure 13:
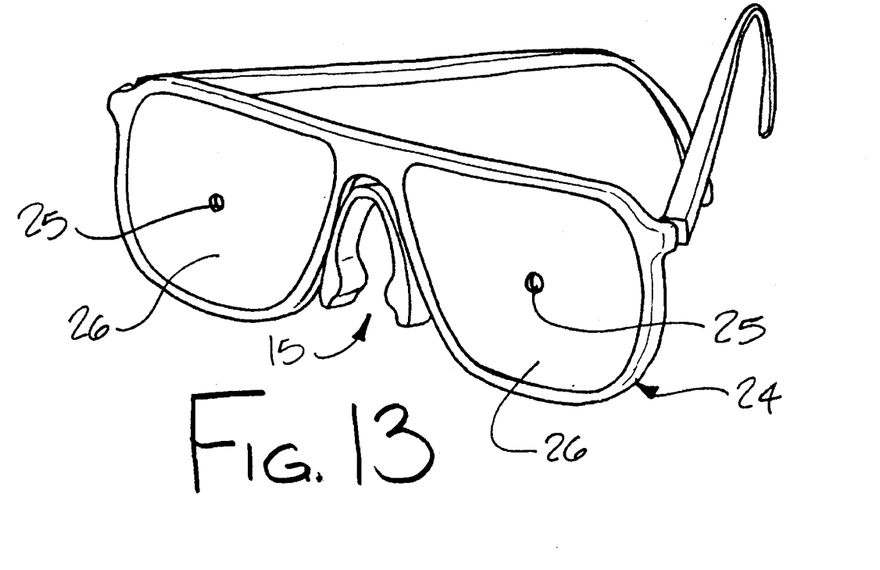
FIG. 13 is a view illustrating the clamp attached to eyeglasses.

The clamp 15 can be attached to eyeglasses 24 (FIG. 13). A special type of eyeglass 24 (known in the art) with holes 25 in the lenses 26 allows eyedrop medication to be applied to the eye through the holes 25. This eyeglass 24 is used to attach clamp 15. The clamp 15 is applied to the bridge of the nose prior to administering the medicament to the eye through the hole 25 in the eyeglasses.

Figure 14:
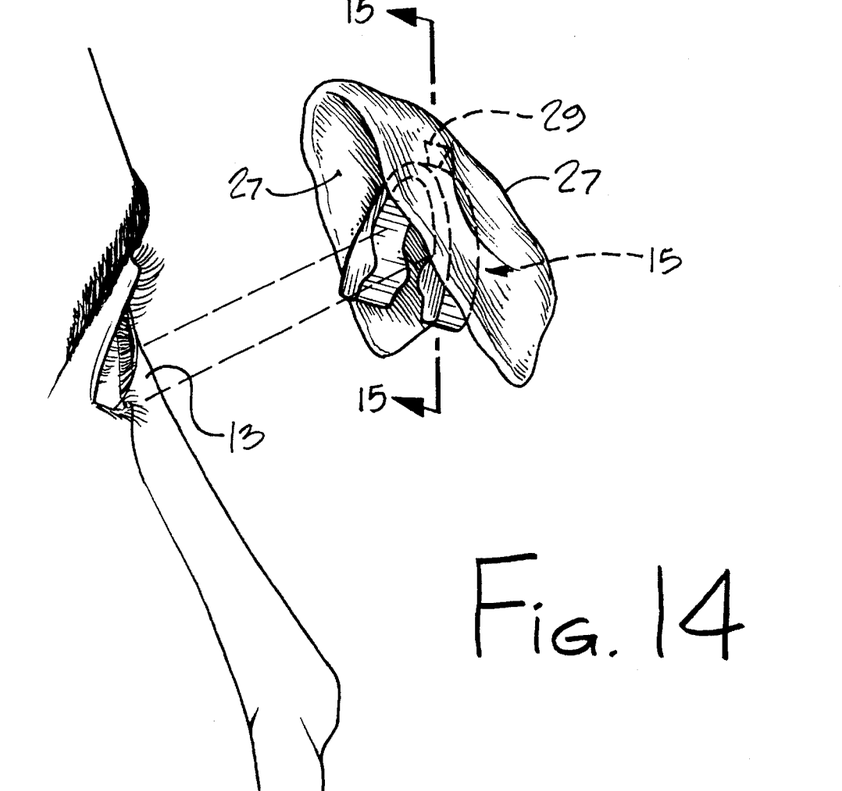
FIG. 14 is a view illustrating the clamp embedded in a flexible molded positioning device.

With reference to FIG. 14 the nasolacrimal clamp 15 is seated in a flexible molded positioning device 27. The flexible molded positioning device 27 containing the clamp 15 is molded to substantially exactly fit the clamp over the bridge of the nose 13 and the fossa of the nasolacrimal sac. The straight dashed lines in FIG. 14 show the direction the clamp 15 will take to the bridge of the nose to seal the nasolacrimal sac and thereby occlude drainage of medicament.

Figure 15:
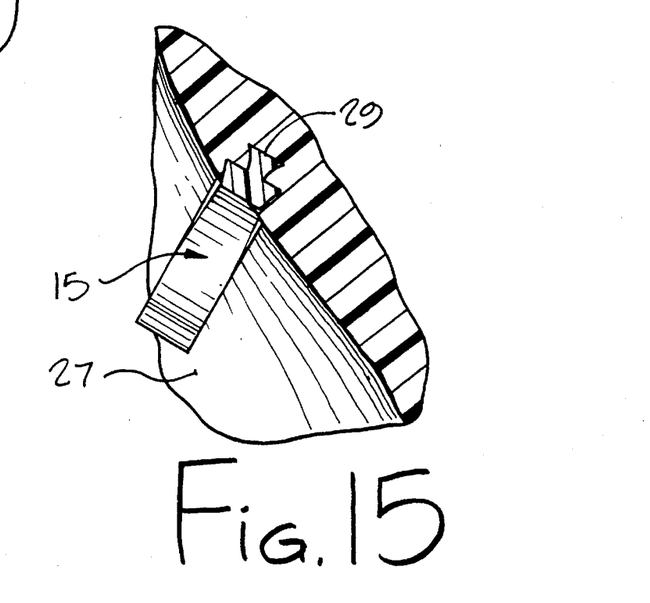
FIG. 15 is a view taken along lines 15—15 of FIG. 14 showing in detail a dove-tail joint used to secure the clamp in the flexible molded positioning device.

More specificaly, with reference to FIG. 15, in a sectional view taken along lines 1–15 of FIG. 14, a dovetail joint 29 is integral with the clamp 15 and is embedded in the flexible molded positioning device 27. This dovetail joint 29 is designed to more effectively secure the clamp 15 in the flexible molded positioning device 27.

Figure 16:
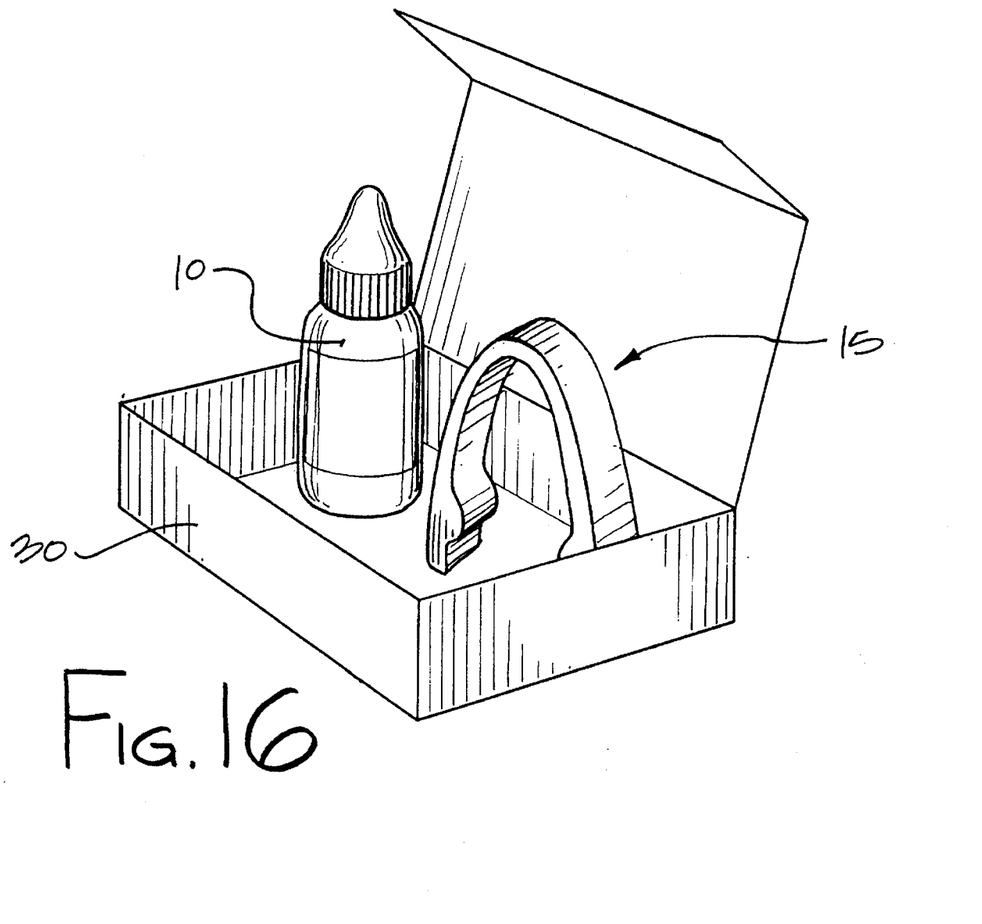
FIG. 16 illustrates a kit or package containing the clamp and a container of eyedrop medication.

With reference to FIG. 16, the invention envisions the clamp 15 being packaged 30 along with the eye drop 10 for dispensing to a patient.

The nasolacrimal occlusion clamp and method of this invention have many advantages over the prior art devices and methods:

1. The device of this invention is superior to manual occlusion because, once the clamp is applied to the bridge of the nose both eyes can be medicated without the need for applying pressure with the fingers. Thus with the clamp in place before applying medication to the eye, contact time between medication and eye is maximized.
2. The clamp of this invention when used to seal drainage has the advantage over the use of plastic or collagen plugs placed into the puncta, because the clamp can be applied easily by the lay person; and does not require the use of a doctor or skilled technician for application.
3. It is quite evident, that the clamp, in its convenience of use, is superior to closing the puncta with cautery or laser. These latter methods require surgery. These processes may not be reversible.
4. The clamping method herein disclosed offers advantage over the eyelid closure method because a more positive and complete occlusion is possible.

Clearly, the clamp herein disclosed presents important advantages over the prior art methods and devices; and offers a significant benefit for the patient receiving eyedrop medication.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A dispensing package for dispensing eyedrop medication comprising a dispensing package containing therein a nasolacrimal clamp embedded in a flexible molded positioning device molded to fit the shape of the bridge of a nose and with the clamp therein positioned to positively seal a nasolacrimal sac thereby preventing drainage of medicament, said dispensing package also containing a container of eyedrop medication and an eyedropper.

2. In a method for applying medication to an eye of a patient, the improvement comprising first providing a nasolacrimal clamp embedded in a flexible molded positioning device molded to fit the shape of the bridge of the nose of the patient, the embedded clamp being positioned to positively seal the nasolacrimal sac thereby preventing drainage of medicament, applying said molded positioning device to the bridge of the nose, and thereafter administering medication to the eye.

3. The method of claim 2 wherein the medication is an eyedrop.

* * * * *